United States Patent
Deshpande (10) Patent No.: US 8,753,300 B2
(45) Date of Patent: Jun. 17, 2014

(54) COMPRESSION GARMENT APPARATUS HAVING BASELINE PRESSURE

(75) Inventor: Manish Deshpande, Canton, MA (US)

(73) Assignee: Covidien LP, Mansfield, MA (US)

( * ) Notice: Subject to any disclaimer, the term of this patent is extended or adjusted under 35 U.S.C. 154(b) by 560 days.

(21) Appl. No.: 12/893,679

(22) Filed: Sep. 29, 2010

(65) Prior Publication Data

US 2012/0078146 A1 Mar. 29, 2012

(51) Int. Cl.
*A61H 9/00* (2006.01)

(52) U.S. Cl.
USPC ............. 601/151; 601/152; 601/148; 602/13; 606/201

(58) Field of Classification Search
USPC ........... 601/23, 24, 26, 27, 33, 35, 75, 84, 85, 601/88, 90, 92, 93, 96, 97, 98, 101, 103, 601/105, 107, 108, 133, 134, 148–152, 601/DIG. 7, DIG. 20; 602/13; 606/201, 202; 128/DIG. 20
See application file for complete search history.

(56) References Cited

U.S. PATENT DOCUMENTS

| | | | |
|---|---|---|---|
| 3,892,229 A | 7/1975 | Taylor et al. | |
| 3,901,221 A | 8/1975 | Nicholson et al. | |
| 4,013,069 A | 3/1977 | Hasty | |
| 4,206,751 A | 6/1980 | Schneider | |
| 4,624,244 A * | 11/1986 | Taheri | 601/152 |
| 4,986,260 A | 1/1991 | Iams et al. | |
| 5,007,411 A | 4/1991 | Dye | |
| 5,109,832 A | 5/1992 | Proctor et al. | |
| 5,117,812 A | 6/1992 | McWhorter | |
| 5,139,475 A * | 8/1992 | Robicsek | 602/13 |
| 5,186,163 A * | 2/1993 | Dye | 601/27 |
| 5,218,954 A | 6/1993 | van Bemmelen | |
| 5,263,473 A | 11/1993 | McWhorter | |
| 5,443,440 A | 8/1995 | Tumey et al. | |
| 5,517,999 A | 5/1996 | Newell | |
| 5,520,622 A | 5/1996 | Bastyr et al. | |
| 5,701,894 A | 12/1997 | Cherry et al. | |
| 5,827,209 A | 10/1998 | Gross | |
| 5,855,589 A | 1/1999 | McEwen et al. | |
| 5,891,065 A | 4/1999 | Cariapa et al. | |
| 5,982,285 A | 11/1999 | Bueche et al. | |

(Continued)

FOREIGN PATENT DOCUMENTS

| | | |
|---|---|---|
| CA | 2411046 C | 11/2008 |
| CN | 1794964 A | 6/2006 |

(Continued)

OTHER PUBLICATIONS

English Translation of Preliminary Rejection issued Nov. 16, 2012 in corresponding Korean Patent Application No. 10-2011-98807, 2 pgs.

(Continued)

*Primary Examiner* — Steven Douglas
(74) *Attorney, Agent, or Firm* — John Paul Mello, Esq.

(57) ABSTRACT

A compression garment apparatus including a compression garment and a pressurizer. The pressurizer intermittently pressurizes a therapeutic bladder on the compression garment and maintains a baseline pressure in the therapeutic bladder to maintain the therapeutic bladder in position with respect to a target compression zone on a body part on which the garment is worn. The baseline pressure is adjusted in response to sensed physical characteristics.

24 Claims, 4 Drawing Sheets

(56) References Cited

U.S. PATENT DOCUMENTS

| | | | |
|---|---|---|---|
| 6,007,559 A | 12/1999 | Arkans | |
| 6,209,144 B1 | 4/2001 | Carter | |
| 6,290,662 B1 | 9/2001 | Morris et al. | |
| 6,306,088 B1 | 10/2001 | Krausman et al. | |
| 6,322,528 B1 | 11/2001 | Kania | |
| 6,338,723 B1 * | 1/2002 | Carpenter et al. | 602/75 |
| 6,368,357 B1 | 4/2002 | Schon et al. | |
| 6,409,691 B1 | 6/2002 | Dakin et al. | |
| 6,494,852 B1 * | 12/2002 | Barak et al. | 601/151 |
| 6,540,707 B1 | 4/2003 | Stark et al. | |
| 6,544,202 B2 | 4/2003 | McEwen et al. | |
| 6,544,203 B2 | 4/2003 | Hazard | |
| 6,558,338 B1 * | 5/2003 | Wasserman | 601/152 |
| 6,656,141 B1 | 12/2003 | Reid | |
| 7,056,297 B2 | 6/2006 | Dohno et al. | |
| 7,204,809 B2 | 4/2007 | Hung | |
| 7,254,516 B2 | 8/2007 | Case, Jr. et al. | |
| 7,270,642 B2 | 9/2007 | Ouchene et al. | |
| 7,503,878 B1 | 3/2009 | Amsbury et al. | |
| 7,811,333 B2 | 10/2010 | Jonsson et al. | |
| 7,871,387 B2 | 1/2011 | Tordella et al. | |
| 7,947,003 B2 * | 5/2011 | Bonnefin et al. | 601/150 |
| 7,967,766 B2 * | 6/2011 | Ravikumar | 602/13 |
| 8,162,861 B2 * | 4/2012 | Avitable et al. | 601/151 |
| 2002/0104535 A1 | 8/2002 | Biondo et al. | |
| 2004/0199090 A1 | 10/2004 | Sanders et al. | |
| 2005/0107725 A1 | 5/2005 | Wild et al. | |
| 2006/0036203 A1 | 2/2006 | Ouchene et al. | |
| 2006/0287621 A1 | 12/2006 | Atkinson et al. | |
| 2007/0049853 A1 | 3/2007 | Adams et al. | |
| 2007/0135742 A1 | 6/2007 | Meyer et al. | |
| 2007/0270665 A1 | 11/2007 | Yang et al. | |
| 2008/0082029 A1 | 4/2008 | Diana | |
| 2008/0125684 A1 | 5/2008 | Nardi et al. | |
| 2008/0132816 A1 | 6/2008 | Kane et al. | |
| 2009/0024062 A1 | 1/2009 | Einarsson | |
| 2009/0076423 A1 | 3/2009 | Reeves et al. | |
| 2009/0088674 A1 | 4/2009 | Caillouette et al. | |
| 2009/0118651 A1 | 5/2009 | Rousso et al. | |
| 2009/0177222 A1 | 7/2009 | Brown et al. | |
| 2010/0010405 A1 | 1/2010 | Nardi et al. | |
| 2010/0081974 A1 | 4/2010 | Vess | |
| 2010/0081977 A1 | 4/2010 | Vess | |
| 2011/0190675 A1 * | 8/2011 | Vess | 601/152 |

FOREIGN PATENT DOCUMENTS

| | | |
|---|---|---|
| CN | 101267793 A | 9/2008 |
| DE | 102006033033 A1 | 1/2008 |
| EP | 1980232 A1 | 10/2008 |
| EP | 2168552 A1 | 3/2010 |
| EP | 2359785 A1 | 8/2011 |
| JP | 07-250875 A | 10/1995 |
| JP | 2000-197675 A | 7/2000 |
| JP | 3107269 U | 1/2005 |
| JP | 2006-521142 A | 9/2006 |
| JP | 2008-136587 A | 6/2008 |
| KR | 10-0918718 A | 10/2008 |
| WO | 0049968 A2 | 8/2000 |

OTHER PUBLICATIONS

English Translation of Notice of Reasons for Rejection mailed Dec. 28, 2012 in corresponding Japanese Patent Application No. 2011-212580, 6 pgs.

European Search Report regarding related application serial No. EP 11182119.5 dated Jan. 31, 2012, 7 pgs.

Exam Report dated Jun. 25, 2012 from related Australian application serial No. 2011224014, 3 pgs.

Canadian Intellectual Property Office, Application No. 2,751,794 Office action dated May 13, 2013, 3 pages, Canada.

Chinese Intellectual Property Office, Application No. 201110303700.4 Office action dated Jun. 9, 2013, 9 pages, China.

Office Action from related Korean Application 10-2011-98807 dated May 27, 2013, 2 pages (English Translation).

* cited by examiner

COMPRESSION GARMENT APPARATUS HAVING BASELINE PRESSURE

FIELD OF THE INVENTION

The present invention generally relates to a compression garment apparatus, and more particularly to a compression garment apparatus having baseline pressure.

BACKGROUND OF THE INVENTION

A major concern for generally immobile patients and like persons are medical conditions that form blood clots, such as, deep vein thrombosis (DVT), and peripheral edema. Such patients and persons include those undergoing surgery, anesthesia, extended periods of bed rest, etc. These blood clotting conditions generally occur in the deep veins of the lower extremities and/or pelvis. These veins, such as the iliac, femoral, popliteal, and tibial return deoxygenated blood to the heart. For example, when blood circulation in these veins is retarded due to illness, injury, or inactivity, there is a tendency for blood to accumulate or pool. A static pool of blood may lead to the formation of a blood clot, which can interfere with cardiovascular circulation. Most seriously, a fragment of the blood clot can break loose and migrate. A pulmonary embolus can form from the fragment potentially blocking a main pulmonary artery, which may be life threatening. The current invention can also be applied to the treatment of other conditions, such as lymphedema.

Conventional vascular compression systems include a compression garment fluidly connected to a controller for cyclically inflating the compression garment. The cyclical inflation of the compression garment enhances blood circulation and decreases the likelihood of DVT. A system of conduits connects the compression garment to the controller. Newer vascular compression garments have portable controllers that are much smaller and even mountable on the compression garment so that the patient may move about freely without having to first remove the compression garment or disconnect the compression garment from a controller. These new compression garments may be worn when a patient is stationary or ambulatory and enhance patient compliance because of convenience of use.

Active compression garments for applying intermittent compression therapy to a body part (e.g., a limb such as a leg) have many applications, including DVT prophylaxis, edema prevention, and aiding in wound healing. The performance of such compression garments is sensitive to the ability of the garment to retain its initial fit or tightness and the inflatable bladders to retain their original position around the body part. This can be very difficult when the compression garments are used during and after ambulation, such as walking, sitting, standing, and rolling over. The garments tend to loosen around the body part or slide down the body part causing misalignment of inflatable bladders with corresponding body parts, which may result in ineffective compression therapy and/or discomfort. The present invention is directed to maintaining desired fit of the garment on the body part and maintaining the inflatable bladders in position with respect to a target compression zone on the body part to improve applied compression therapy.

SUMMARY OF THE INVENTION

One aspect of the present invention is directed to a compression garment apparatus including a compression garment including an inflatable therapeutic bladder. The compression garment is selectively positionable on a body part so the therapeutic bladder covers a target compression zone on the body part. The compression garment apparatus further includes a pressurizer operatively connectable to the therapeutic bladder for selectively pressurizing the therapeutic bladder by increasing gas pressure within the therapeutic bladder to provide therapeutic compression therapy to the target compression zone on the body part. The pressurizer includes a sensor for sensing and generating signals representative of at least one physical characteristic selected from a group of characteristics consisting of an orientation of the body part, a motion of the body part, an acceleration of the body part, and a motion of the garment relative to the target compression zone. The pressurizer also includes a controller operatively connected to the sensor. The controller executes a compression regimen including successive compression cycles to provide intermittent compression therapy to the compression zone. The compression cycles each include an inflation phase during which the controller directs pressurized gas to the therapeutic bladder and a vent phase during which the controller allows gas to vent from the therapeutic bladder. The controller maintains a baseline pressure in the therapeutic bladder to maintain the therapeutic bladder in position with respect to the target compression zone. The controller adjusts the baseline pressure in response to signals received from the sensor representing the physical characteristic.

Another aspect of the invention is directed to a method of applying compression therapy on a target compression zone of a body part of a human. The method includes covering the target compression zone of the body part with a compression garment having an inflatable therapeutic bladder. The method further includes repeatedly directing pressurized gas to the therapeutic bladder and venting gas from the therapeutic bladder to provide intermittent compression therapy to the target compression zone. The method also includes sensing at least one characteristic selected from a group of characteristics consisting of an orientation of the body part, a motion of the body part, an acceleration of the body part, and a motion of the garment relative to the target compression zone. A baseline pressure is maintained in the therapeutic bladder to maintain the therapeutic bladder in position with respect to the target compression zone. The baseline pressure is adjusted in response to signals received from the sensor representing the physical characteristic.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Referring to the drawings and in particular to FIGS. 1-4, a compression garment apparatus for applying compression therapy to a body part of a wearer is generally indicated by the reference number 20. As will be explained in detail hereinafter, the compression garment apparatus 20 may be used for intermittently or cyclically compressing a body part such as a limb (e.g., a leg or arm). The body part referred to herein and shown throughout the drawings is a leg, generally designated by L.

The compression garment apparatus 20 includes a compression garment, generally indicated by 22, and a pressurizer, generally indicated by 24. The compression garment 22 includes three therapeutic bladders 26A-26C. As described in more detail below, the pressurizer 24 intermittently pressurizes the bladders 26A-26C to impart compression therapy on the body part L and maintains a baseline pressure in the bladders 26A-26C to maintain the bladders in position with respect to the body part. The pressurizer 24 is operatively connected to the bladders 26A-26C such as by conduits 30 (FIG. 1) for inflating the bladders. The illustrated pressurizer 24 is mounted on the compression garment 22. An alternative embodiment in which a pressurizer is removably mounted on a compression garment and operatively connected to bladders on the compression garment is disclosed in more detail in U.S. patent application Ser. Nos. 12/241,670 and 12/241,936, both of which are assigned to Tyco Healthcare Group LP and incorporated by reference in their entireties. Other embodiments, such as where the pressurizer 24 is not configured for mounting on the compression garment 22, are within the scope of the present invention.

Figure 1:
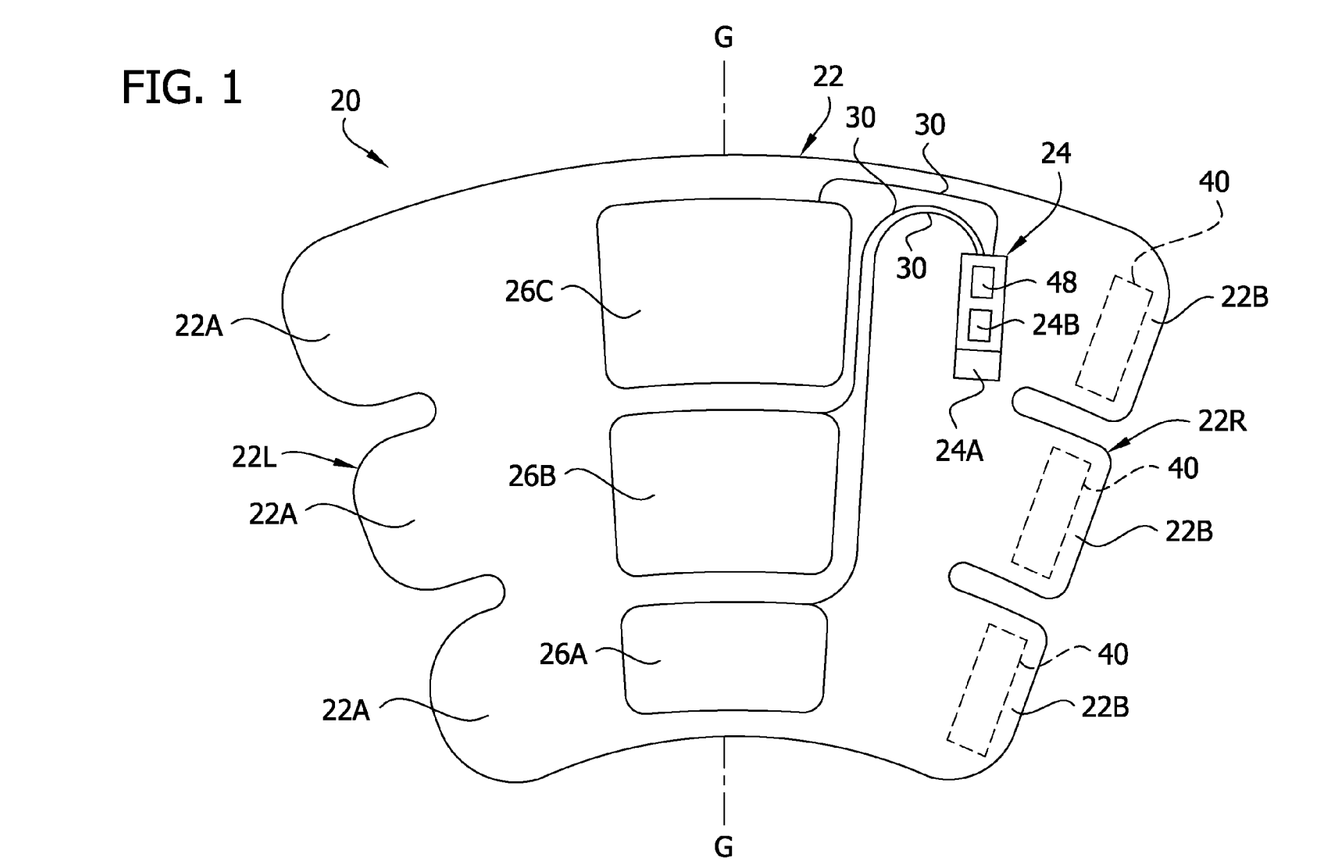
FIG. 1 is a schematical plan view of a compression garment apparatus of the present invention shown in an open, unwrapped configuration.
Figure 2:
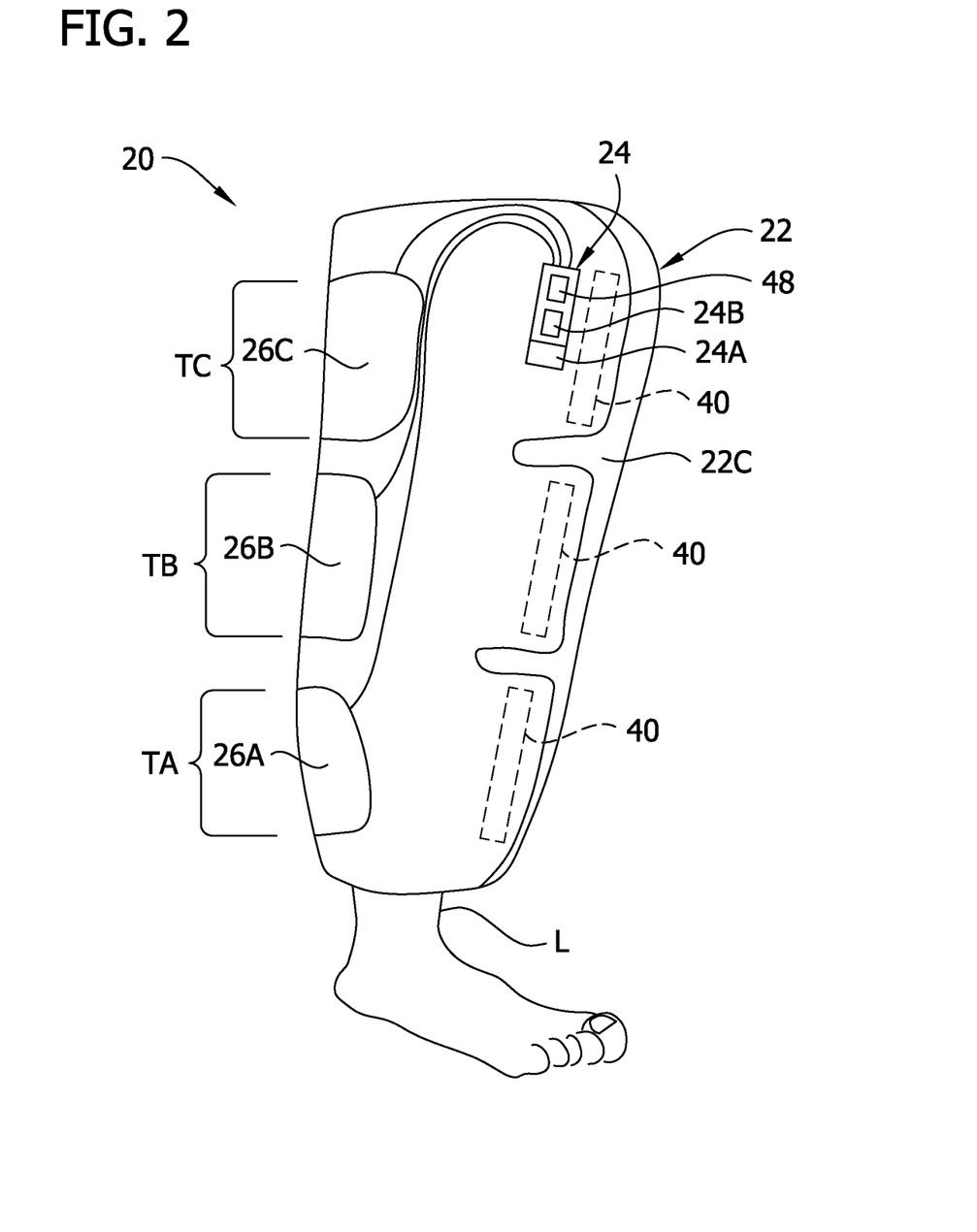
FIG. 2 is a schematical side perspective of the compression garment apparatus wrapped on a leg in an upright orientation.

As shown in FIG. 2, the compression garment 22 is selectively positionable on the body part L so that the therapeutic bladders 26A-26C cover or overlie respective target compression zones TA-TC on the body part. The target compression zones TA-TC may be any portions of the body part L upon which it is desired to impart compression therapy. For example, a target compression zone on the leg may comprise generally a rear side of the leg L or a particular portion thereof such as the calf or the rearward part of the thigh. The rear side of the leg L includes calf and thigh muscles through which veins pass and compression of which enhances flow of blood in those veins. Other target compression zones may be used such as a larger portion of the leg.

The illustrated compression garment 22 has a "thigh length" size, i.e., the compression garment extends generally from the ankle to the thigh. As shown in FIG. 2, the therapeutic bladders 26A-26C are positioned on the garment 22 to generally overlie the rear side of the leg L, and more particularly, the ankle, calf, and thigh, respectively. The three therapeutic bladders 26A-26C are arranged in sequence along the leg L. Other sizes and shapes of garments (e.g., "knee length," extending generally from the ankle to below the knee) or having different configurations of therapeutic bladders (e.g., one, two, or more therapeutic bladders) are also envisioned as being within the scope of the present invention.

The compression garment 22 may be placed in a self-retaining configuration on the leg L by positioning the therapeutic bladders 26A-26C over the desired target compression zones TA-TC and wrapping the compression garment around the leg such that opposite sides of the compression garment 22L, 22R (FIG. 1) overlap each other. A generally tight or snug fit is desirable so that pressurization of the therapeutic bladders 26A-26C causes compression of the body part L. The illustrated compression garment 22 includes corresponding flaps 22A, 22B on each side 22L, 22R of the compression garment to facilitate tightening and securing of the compression garment. The compression garment 22 is tightened around the leg L by pulling and overlapping the opposite sides 22L, 22R of the compression garment. The compression garment 22 may be secured about the leg L by fasteners 40. For example, the fasteners 40 in the illustrated embodiment comprise sections of hook fabric (also designated 40) on the flaps 22B for fastening to loop fabric on an outside surface of the compression garment 22C (FIG. 2). Compression garments having other retention configurations capable of selective positioning on a body part for placement of a therapeutic bladder with respect to a target compression zone are within the scope of the present invention.

The compression garment 22 may be constructed in various ways known in the art. In one construction, the garment 22 is formed of opposing inner and outer sheets of a generally flexible, fluid impervious material (e.g., PVC) that are welded together along bladder weld lines to form the bladders 26A-26C. Alternatively, the bladders 26A-26C may be formed separately and mounted on the compression garment 22.

The pressurizer 24 intermittently pressurizes the bladders 26A-26C by introducing gas into the bladders, increasing the gas pressure in the bladders to provide therapeutic compression therapy to the target compression zones TA-TC on the leg L. The pressurizer 24 includes apparatus for pressurizing or compressing gas 24A (e.g., a battery-powered pump) and a controller 24B for directing the pressurized gas to the bladders 26A-26C as desired. The controller 24B may include a microprocessor and suitable valving (not shown).

The controller 24B may be programmed to execute various compression regimens. For example, the controller 24B may execute a compression regimen including successive compression cycles to provide intermittent compression therapy to the target compression zones TA-TC. The compression cycles each include an inflation phase and a vent phase. Successive compression cycles may be separated by a time period. The controller 24B maintains a baseline pressure in the bladders 26A-26C between compression cycles (i.e., between the vent phase of a first inflation cycle and an inflation phase of a second inflation cycles) to maintain the bladders in position with respect to the target compression zones TA-TC.

During the inflation phase, the controller 24B directs pressurized gas to the bladders 26A-26C to achieve a therapeutic pressure in each of the bladders. The therapeutic pressure may be the same or be different in each bladder. The controller 24B may direct pressurized gas to the bladders 26A-26C to pressurize the bladders in sequence (e.g., ankle to thigh) to peristaltically enhance flow of bodily fluids. The controller 24B may be configured and programmed to execute various other inflation phases, all of which are within the scope of the present invention.

During the vent phase, the controller allows gas to vent from the therapeutic bladders 26A-26C. The bladders 26A-26C may be vented simultaneously, in sequence, or in another order. For example, the vent phase is initiated by opening valving on the pressurizer 24 to allow gas to vent from the bladders 26A-26C to atmosphere. The vent phase ends when the valving is closed. The controller 24B maintains a baseline pressure in the bladders 26A-26C by closing the valving while some pressure remains in the bladders. The baseline pressure is maintained in the bladders 26A-26C until the next inflation phase begins. The baseline pressure may be the same in each of the bladders 26A-26C (e.g., about 6 mm Hg). Alternatively, the baseline pressure may be different in each bladder 26A-26C. For example, the baseline pressure may be about 8 mm Hg in the ankle bladder 26A, about 6 mm Hg in the calf bladder 26B, and about 4 mm Hg in the thigh bladder 26C.

The baseline pressure in the bladders 26A-26C provides structural support to the compression garment 22. The baseline pressure provides rigidity to the compression garment 22 relative to the general flexible nature of the garment. For example, the baseline pressure may provide sufficient rigidity to the compression garment 22 to cause the compression garment to "stay up" on the leg (i.e., not "fall down" onto itself) when the wearer is standing. However, the baseline pressure desirably is prevented from exceeding a pressure at which the support bladder is generally compliant to movement of the body part L. In other words, the baseline pressure does not impede general movement of the leg L such as bending at the knee. The baseline pressure maintains inside surfaces of the compression garment 22 in contact with the leg L to provide friction for preventing the compression garment from slipping on the leg. The bladders 26A-26C may be configured to expand inwardly toward the leg L to fill space between the leg and the compression garment to create a tighter fit. The tighter fit increases friction between the compression garment 22 and the leg L.

The baseline pressure desirably is adjusted as necessary to maintain the bladders 26A-26C in place with respect to the target compression zones TA-TC. Maintaining a high baseline pressure in the bladders 26A-26C for extended time periods (e.g., an extended time period between two successive inflation cycles or an extended time period between several successive inflation cycles) may cause discomfort to the wearer. For example, the extended time period may include time between only two successive inflation cycles or time between several successive inflation cycles. Such discomfort may result from pressure causing skin irritation or pressure on the leg L that becomes uncomfortable after extended exposure. Moreover, the tight fit caused by the baseline pressure may hinder air circulation between the garment and the leg L, causing retention of body heat and possible accumulation of perspiration. Accordingly, it is desirable to adjust the baseline pressure in various circumstances. For example, baseline pressure may be maintained or even increased in situations when needed, and decreased or not maintained when the baseline pressure is generally not necessary.

To facilitate adjustment of the baseline pressure, the pressurizer 24 includes one or more sensors 48 operatively connected to the controller 24B. The sensor 48 senses physical characteristics relevant to adjustment of the baseline pressure. For example, the sensor 48 may be adapted to sense orientation of the body part L, motion of the body part, acceleration of the body part, or motion of the garment 22 relative to one or more target compression zones TA-TC. Such characteristics are explained in more detail below. The sensor 48 generates signals indicating such characteristics. These signals are communicated to the controller 24B. The controller 24B adjusts the baseline pressure depending at least in part on signals received from the sensor 48. The illustrated sensor 48 is provided on the pressurizer 24, but the sensor 48 may be separate from the pressurizer and mounted separately on the compression garment 22 or located elsewhere on the wearer. Various types of sensors 48 may be used. For example, accelerometers and other sensors based on capacitive, piezoresistive, piezoelectric, Hall effect, magnetorestrictive, resonant beam, or other technologies may be used.

Figure 3:
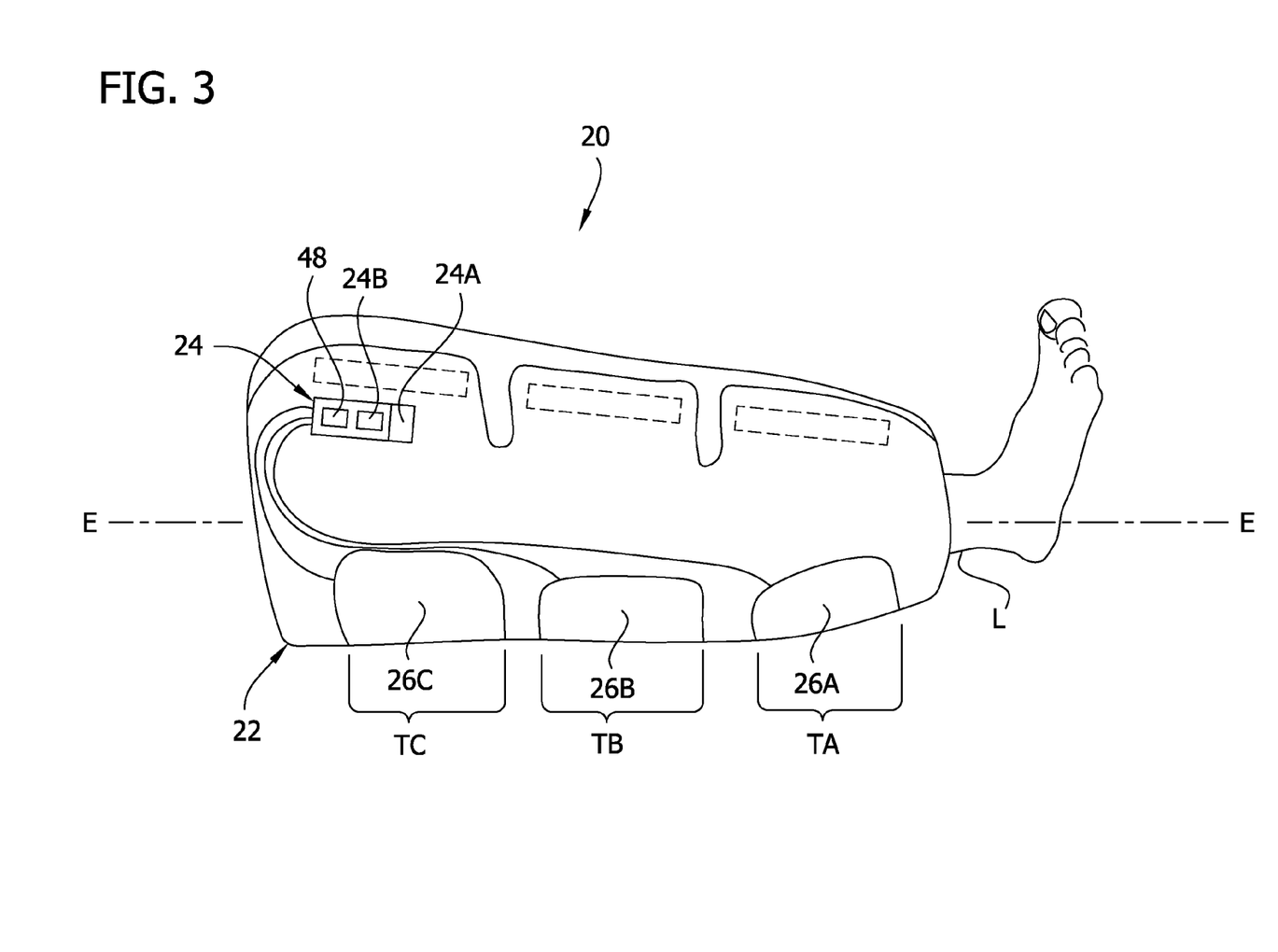
FIG. 3 is a schematical side elevation of the apparatus wrapped on the leg in a generally horizontal orientation.

In FIG. 3, the leg L is shown in a generally horizontal orientation. In such an orientation, the baseline pressure may be generally minimal or zero. The orientation of the leg L in FIG. 3 represents a possible orientation of the leg when the wearer is lying in a bed. In this orientation, a baseline pressure that is minimal or zero may be sufficient to maintain the desired fit of the garment 22 on the leg L or the desired position of the therapeutic bladder 26A-26C with respect to the target compression zones TA-TC. If the wearer were to, for example, roll over in bed or change the orientation of their leg L, increased baseline pressure may be desirable to prevent the therapeutic bladders 26A-26C from moving with respect to the target compression zones TA-TC.

Figure 4:
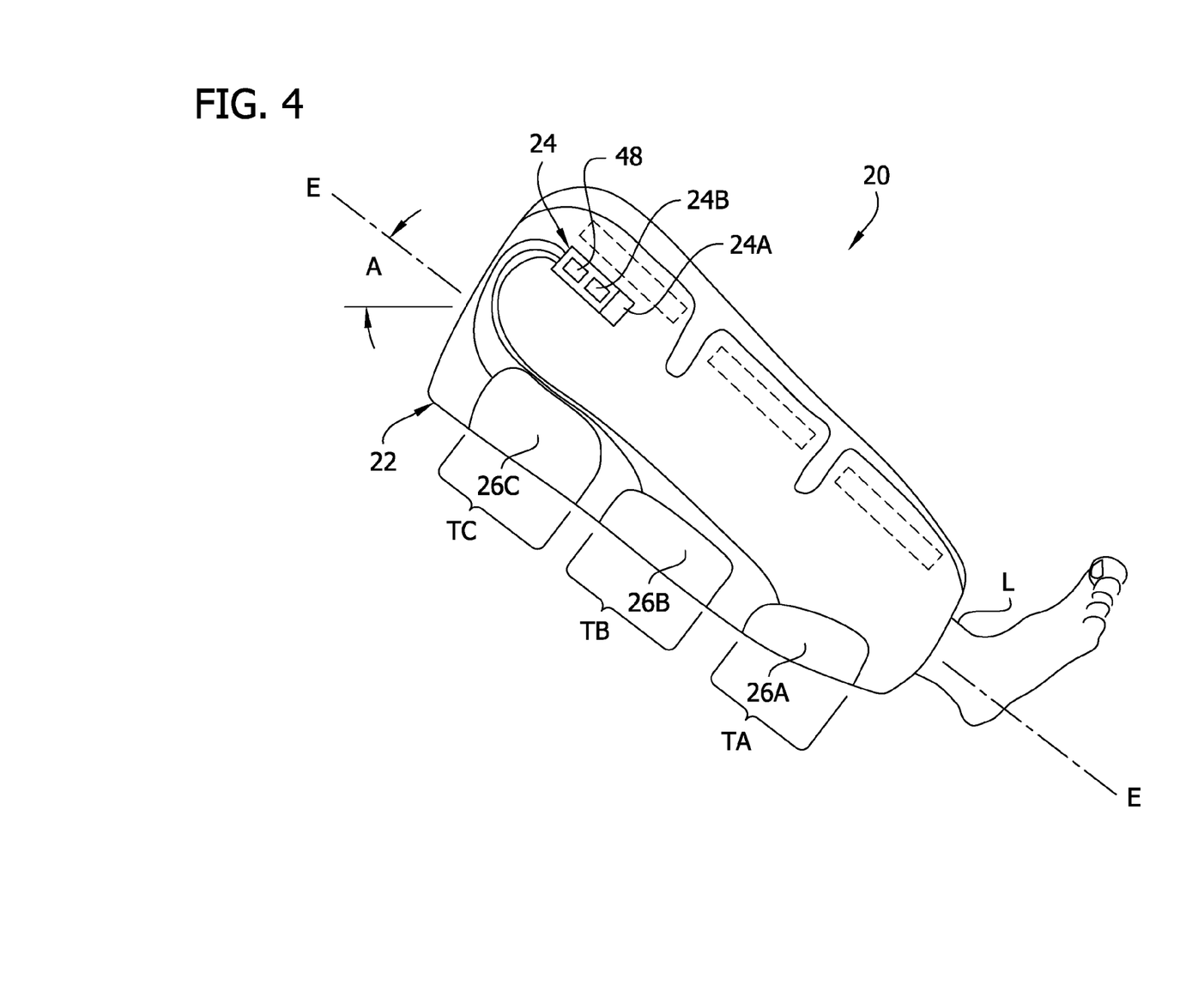
FIG. 4 is a schematical side elevation of the apparatus wrapped on the leg in an inclined orientation.

FIGS. 2 and 4 show the leg L in orientations in which it may be desirable to maintain an increased baseline pressure in the bladders 26A-26C. The controller 24B may increase the baseline pressure based on sensed limb orientation. For example, the controller 24B may increase the baseline pressure in response to a signal received from the sensor 48 indicating the orientation of the body part L is beyond a threshold orientation or outside a predetermined orientation range. The baseline pressure may be increased when the longitudinal axis E-E of the leg is at least 30 degrees with respect to horizontal (e.g., angle A in FIG. 4). Other threshold orientations may be used, such as 40, 50, 60, 70, or 80 degrees with respect to horizontal. Alternatively, the baseline pressure may be increased when the longitudinal axis E-E of the leg is outside a predetermined orientation range such as 0-30, 0-40, 0-50, 0-60, 0-70, or 0-80 degrees with respect to horizontal. Moreover, the baseline pressure may be increased when the sensor 48 indicates the leg L is generally upright (e.g., as shown in FIG. 2), and the baseline pressure may be decreased when the leg is recumbent (e.g., as shown in FIG. 3). The tilt angle of the body part L may be determined using an accelerometer as the sensor 48. Signals from the accelerometer 48 are filtered using software or hardware to recognize acceleration due to tilt angle, which is measured and evaluated by the controller 24B. The sensor 48 may also be used to sense angular configuration of the leg L (i.e., bending at the knee), in which case two sensors 48 may be necessary. For example, a first sensor may be positioned adjacent the thigh portion, a second sensor may be positioned adjacent the ankle portion, and proximity of the two sensors may be monitored to determine angle (not shown). The baseline pressure may be reduced when orientation of the leg L approaches horizontal or after the leg remains generally horizontal for a predetermined amount of time.

The controller 24B may also adjust the baseline pressure based on sensed movement of the garment 22 relative to the target compression zones TA-TC. For example, the sensor 48 may be adapted to sense motion of the garment 22 longitudinally or circumferentially about the leg L. Such a sensor 48 may be positioned on an inside surface of the compression garment (not shown) to sense movement along the surface of the leg L. In response to sensed movement of the garment 22 relative to the target compression zones TA-TC, the baseline pressure in one or more of the bladders 26A-26C may be adjusted. For example, if movement of the ankle bladder 26A with respect to the leg L is sensed, the baseline pressure may be increased in only the ankle bladder, multiple bladders 26A-26C, or all of the bladders. Moreover, two sensors 48 may be used, for example, one on the garment and one elsewhere on the wearer, and the positions of the sensors may be monitored with respect to each other. Such an arrangement could be used to monitor motion in the form of bending at the knee.

The controller 24B may also adjust the baseline pressure depending on sensed limb movement or acceleration. The need for the compression garment 22 to have a good fit on the leg L is increased when the wearer is moving in bed or ambulating because the garment may tend to slip or slide on the leg during movement of the leg. The controller 24B may increase the baseline pressure in response to a signal received from the sensor 48 indicating the motion or acceleration of the body part L is beyond a threshold amount of motion or acceleration or outside a predetermined acceleration range. For example, the baseline pressure may be increased when the sensor 48 indicates the limb L is moving more than a predetermined minimum amount. Moreover, the baseline pressure may be increased when the sensor 48 indicates the wearer is ambulating. For example, the sensor 48 may be an accelerometer and the controller 24B may be programmed to determine when the wearer is walking by "step counting," where the controller 24B recognizes a step each time a change in slope of the longitudinal axis acceleration occurs. Alternatively, a GPS tracker 48 may be used for sensing movement and triggering increase of the baseline pressure based on movement. Other types of sensors may be used to detect motion and acceleration. The baseline pressure may be reduced immediately or a predetermined amount of time after movement or acceleration is no longer sensed.

As used herein, "the baseline pressure" refers collectively to the baseline pressures maintained in each of the bladders 26A-26C. Reference to "the baseline pressure" is not necessarily a reference to a singular baseline pressure. As described above, the baseline pressure may be different in each bladder 26A-26C. For example, the baseline pressure in distal bladders may be more than the baseline pressure in proximal bladders. Moreover, during any given time period, a baseline pressure may be maintained in one or more bladders 26A-26C but not the other of the bladders. In addition, reference to adjustment of the baseline pressure means the baseline pressure in one or more of the bladders 26A-26C is adjusted. The controller 24B may independently adjust the baseline pressure in each of the bladders 26A-26C. Based on the sensed physical characteristic, the baseline pressure in one or more of the bladders 26A-26C may be adjusted the same amount or different amounts. Adjusting the baseline pressure may mean that the baseline pressure in one of the bladders 26A-26C is increased while the baseline pressure in others of the bladders is decreased. Baseline pressure may be adjusted incrementally. For example, the baseline pressure may be increased by 0.5 or 1 mmHg for every increment of change of orientation (e.g., every 10 degrees) with respect to horizontal, for incremental changes in magnitude or speed of movement (e.g., every 0.1 meters per second), or for incremental changes in acceleration.

The baseline pressure in one or more of the bladders 26A-26C may be adjusted continuously or periodically. For example, the baseline pressure may be adjusted real-time in response to signals received from the sensor 48. In such a case, the baseline pressure may be adjusted continuously during a time period between two successive compression cycles by increasing and decreasing the baseline pressure between the compression cycles as necessary. The controller may determine during any part of a compression cycle or between compression cycles whether to adjust the baseline pressure. Alternatively, the baseline pressure may be adjusted periodically during the compression regimen. For example, the baseline pressure to be maintained in each of the bladders 26A-26C may be determined at a predetermined time during every compression cycle, every other compression cycle, between compression cycles, or at some other periodic rate.

In a cycle of use, the compression garment apparatus 20 is placed on a body part such as the leg L, with the therapeutic bladders 26A-26C covering or overlying the desired target compression zones TA-TC. The pressurizer 24 intermittently pressurizes the therapeutic bladders 26A-26C to impart compression therapy. The controller 24B repeatedly directs pressurized gas to the bladders 26A-26C and vents gas from the bladders to provide intermittent compression therapy on the target compression zone. The pressurizer 24 maintains a baseline pressure in the bladders 26A-26C to maintain the bladders in position with respect to the target compression zones TA-TC. The baseline pressure is adjusted as outlined above in response to signals from the sensor 48 representing physical characteristics.

Having described the invention in detail, it will be apparent that modifications and variations are possible without departing from the scope of the invention defined in the appended claims.

When introducing elements of the present invention or the preferred embodiments(s) thereof, the articles "a", "an", "the", and "said" are intended to mean that there are one or more of the elements. The terms "comprising", "including", and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A compression garment apparatus comprising:
   a compression garment including an inflatable therapeutic bladder, the compression garment being selectively positionable on a body part so the therapeutic bladder covers a target compression zone on the body part; and
   a pressurizer operatively connectable to the therapeutic bladder for selectively pressurizing the therapeutic bladder by increasing gas pressure within the therapeutic bladder to provide therapeutic compression therapy to the target compression zone on the body part, the pressurizer including:
   a sensor for sensing and generating signals representative of at least one physical characteristic selected from a group of characteristics consisting of an orientation of the body part, a motion of the body part, an acceleration of the body part, and a motion of the garment relative to the target compression zone; and
   a controller operatively connected to the sensor, the controller executing a compression regimen including successive compression cycles to provide intermittent compression therapy to the compression zone, the compression cycles each including an inflation phase during which the controller directs pressurized gas to the therapeutic bladder and a vent phase during which the controller allows gas to vent from the therapeutic bladder, the controller maintaining a baseline pressure in the therapeutic bladder to maintain the therapeutic bladder in position with respect to the target compression zone, the controller adjusting the baseline pressure in response to signals received from the sensor representing the physical characteristic.

2. A compression garment apparatus as set forth in claim 1 wherein the controller adjusts the baseline pressure periodically during the compression regimen.

3. A compression garment apparatus as set forth in claim 2 wherein the controller determines during each compression cycle based on the sensed physical characteristic whether to adjust the baseline pressure.

4. A compression garment apparatus as set forth in claim 1 wherein the controller increases the baseline pressure in response to a signal received from the sensor indicating the orientation of the body part is outside a predetermined orientation range.

5. A compression garment apparatus as set forth in claim 1 wherein the controller increases the baseline pressure in response to a signal received from the sensor indicating the motion of the body part is beyond a threshold amount of motion.

6. A compression garment apparatus as set forth in claim 1 wherein the controller decreases the baseline pressure in response to a signal received from the sensor representing the orientation of the body part being recumbent.

7. A compression garment apparatus as set forth in claim 1 wherein the controller increases the baseline pressure in response to a signal received from the sensor indicating the acceleration of the body part is outside a predetermined acceleration range.

8. A compression garment apparatus as set forth in claim 1 wherein:
the therapeutic bladder is a first therapeutic bladder and the compression garment apparatus further comprises second and third therapeutic bladders, the first, second, and third therapeutic bladders being arranged in sequence on the compression garment; and
the controller during each inflation phase sequentially directs compressed gas to each therapeutic bladder to provide intermittent compression therapy to the target compression zone to peristaltically enhance flow of bodily fluids in the body part.

9. A compression garment apparatus as set forth in claim 8 wherein the controller maintains a baseline pressure in each of the first, second, and third therapeutic bladders.

10. A compression garment apparatus as set forth in claim 9 wherein the baseline pressure maintained in each of the three separate therapeutic bladders is adjusted by the controller in response to signals received from the sensor representing the physical characteristic.

11. A method of applying compression therapy on a target compression zone of a body part of a human comprising:
covering the target compression zone of the body part with a compression garment having an inflatable therapeutic bladder;
repeatedly directing pressurized gas to the therapeutic bladder and venting gas from the therapeutic bladder to provide intermittent compression therapy to the target compression zone;
sensing at least one physical characteristic selected from a group of characteristics consisting of an orientation of the body part, a motion of the body part, an acceleration of the body part, and a motion of the garment relative to the target compression zone;
maintaining a baseline pressure in the therapeutic bladder to maintain the therapeutic bladder in position with respect to the target compression zone; and
adjusting the baseline pressure in response to signals received from a sensor representing the physical characteristic.

12. A method as set forth in claim 11 wherein adjusting the baseline pressure comprises periodically adjusting the baseline pressure during the compression regimen.

13. A method as set forth in claim 12 further comprising determining based on the sensed physical characteristic whether to adjust the baseline pressure while at least one of directing pressurized gas to the therapeutic bladder and venting gas from the therapeutic bladder.

14. A method as set forth in claim 11 wherein adjusting the baseline pressure comprises increasing the baseline pressure in response to sensing the motion of the body part being beyond a threshold amount of motion.

15. A method as set forth in claim 11 wherein the body part is a leg and adjusting the baseline pressure comprises increasing the baseline pressure in response to sensing the orientation of the leg being generally upright.

16. A method as set forth in claim 11 wherein the body part is a leg and adjusting the baseline pressure comprises increasing the baseline pressure in response to sensed motion of the leg indicating the human is ambulating.

17. A method as set forth in claim 11 wherein adjusting the baseline pressure comprises reducing pressure in the therapeutic bladder in response to sensing the orientation of the body part being outside a predetermined orientation range.

18. A method as set forth in claim 11 wherein adjusting the baseline pressure comprises increasing the baseline pressure in response to the acceleration of the body part being outside a predetermined acceleration range.

19. A method as set forth in claim 11 wherein adjusting the baseline pressure comprises decreasing the baseline pressure in response to sensing the body part being recumbent.

20. A method as set forth in claim 11 wherein the therapeutic bladder is a first therapeutic bladder and the compression garment includes second and third therapeutic bladders, the first, second, and third therapeutic bladders being arranged in sequence on the body part, and wherein the method comprises sequentially directing compressed gas to each of the therapeutic bladders and venting compressed gas from the therapeutic bladders to apply intermittent therapy on the compression zone to peristaltically enhance flow of bodily fluids in the body part.

21. A compression garment apparatus as set forth in claim 1 wherein the sensor comprises at least one orientation, motion, acceleration, or position sensor.

22. A compression garment apparatus as set forth in claim 1 wherein the controller maintains a baseline pressure in the therapeutic bladder between compression cycles to maintain the therapeutic bladder in position with respect to the target compression zone, and the controller adjusts the predetermined baseline pressure in response to signals received from the sensor representing the physical characteristic.

23. A method as set forth in claim 11 wherein sensing the at least one physical characteristic comprises sensing using at least one orientation, motion, acceleration, or position sensor.

24. A method as set forth in claim 11 wherein maintaining the baseline pressure comprises maintaining a predetermined baseline pressure in the therapeutic bladder, and wherein adjusting the baseline pressure comprises adjusting the predetermined baseline pressure.

* * * * *